(12) United States Patent
Oishi et al.

(10) Patent No.: US 10,765,395 B2
(45) Date of Patent: Sep. 8, 2020

(54) MEDICAL IMAGING DIAGNOSIS APPARATUS AND SCAN PLANNING DEVICE

(71) Applicant: Canon Medical Systems Corporation, Otawara-shi (JP)

(72) Inventors: Keisuke Oishi, Nasushiobara (JP); Hiroki Osaki, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 43 days.

(21) Appl. No.: 16/154,766

(22) Filed: Oct. 9, 2018

(65) Prior Publication Data
US 2019/0105010 A1 Apr. 11, 2019

(30) Foreign Application Priority Data

Oct. 10, 2017 (JP) .................................. 2017-197100
Oct. 5, 2018 (JP) .................................. 2018-189642

(51) Int. Cl.
*A61B 6/00* (2006.01)
*A61B 6/03* (2006.01)
*A61B 6/04* (2006.01)
*A61B 5/055* (2006.01)

(52) U.S. Cl.
CPC .............. *A61B 6/548* (2013.01); *A61B 6/032* (2013.01); *A61B 6/0407* (2013.01); *A61B 6/0457* (2013.01); *A61B 6/4266* (2013.01); *A61B 6/54* (2013.01); *A61B 6/547* (2013.01); *A61B 5/055* (2013.01); *A61B 6/4435* (2013.01); *A61B 6/467* (2013.01); *A61B 6/545* (2013.01)

(58) Field of Classification Search
CPC ........ A61B 6/548; A61B 6/032; A61B 6/0407
See application file for complete search history.

(56) References Cited

U.S. PATENT DOCUMENTS

2010/0299014 A1  11/2010  Bouvier
2014/0210470 A1*  7/2014  Xu .......................... G01R 33/28
                                                         324/309

FOREIGN PATENT DOCUMENTS

JP    2011-229900    11/2011
JP    2017-064400    4/2017

\* cited by examiner

*Primary Examiner* — Hugh Maupin
(74) *Attorney, Agent, or Firm* — Oblon, McClelland, Maier & Neustadt, L.L.P.

(57) ABSTRACT

One embodiment, a medical imaging diagnosis apparatus includes a gantry, a bed and a processing circuitry. The gantry acquires data. The bed supports a table top such that the table top is horizontally and vertically movable relative to a floor surface. The processing circuitry determines a lift route of the table top from an initial height to a target height to be either a first route or a second route. The first route is in which the table top is vertically lifted relative to the floor surface from the initial height to the target height. The second route is in which the table top is vertically lifted, while being horizontally moved, relative to the floor surface from the initial height to the target height.

17 Claims, 11 Drawing Sheets

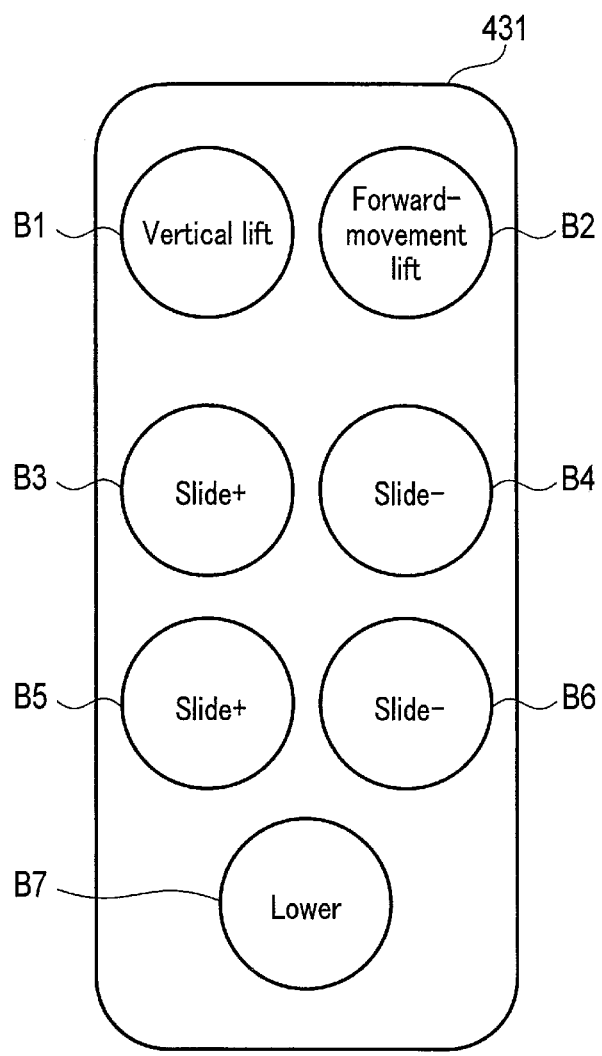
F I G. 8

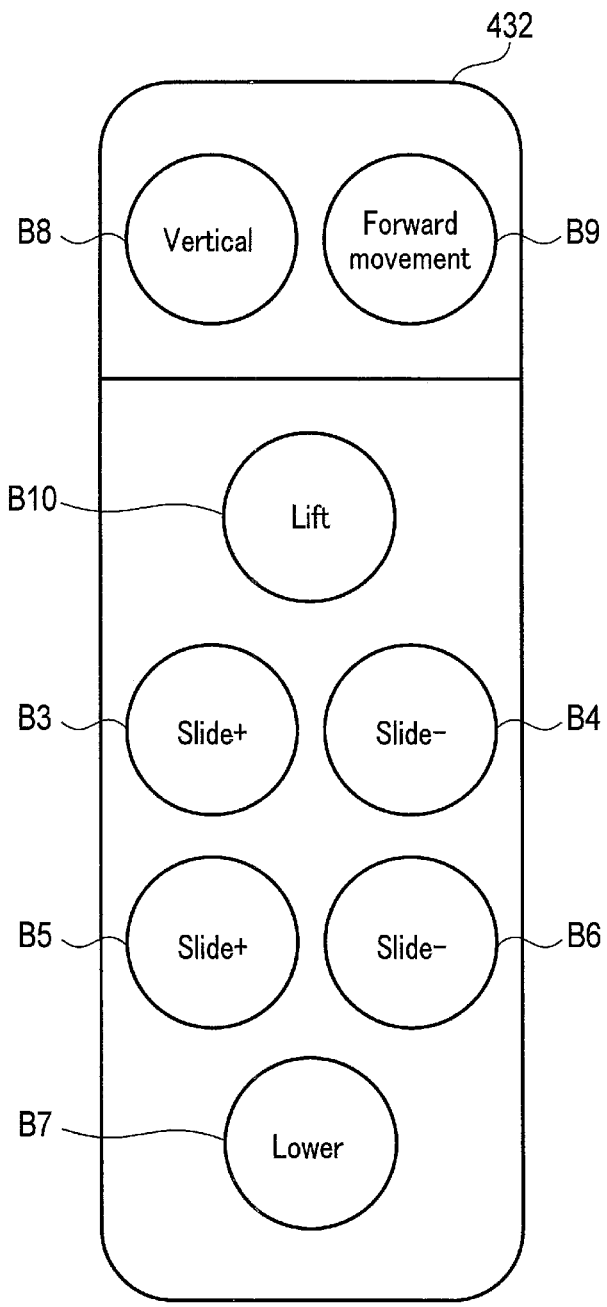
F I G. 9

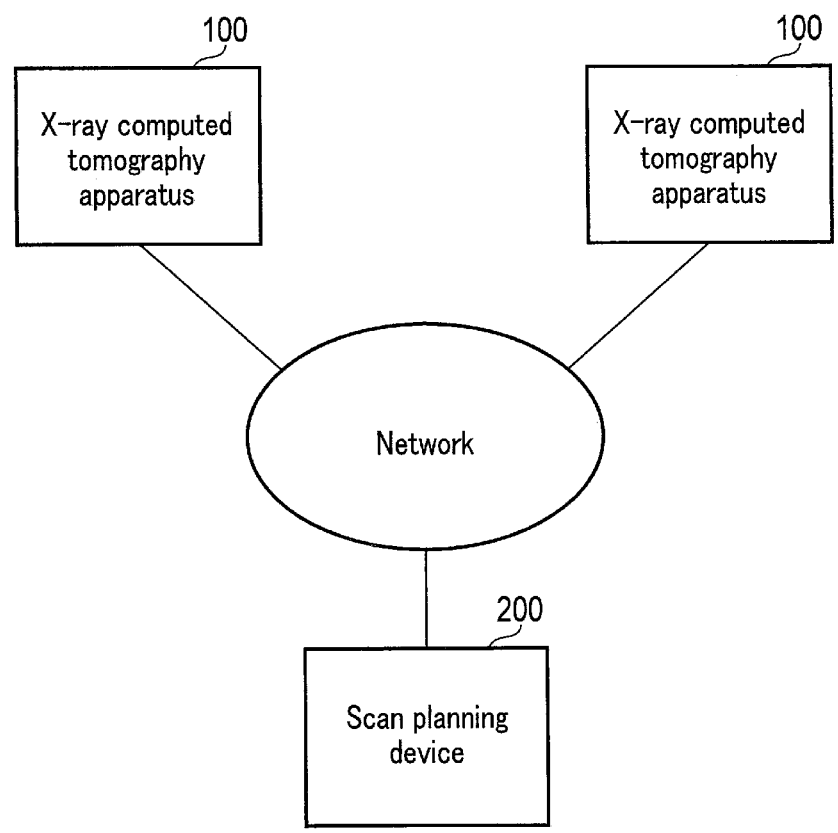
F I G. 10

MEDICAL IMAGING DIAGNOSIS APPARATUS AND SCAN PLANNING DEVICE

CROSS-REFERENCE TO RELATED APPLICATIONS

This application is based upon and claims the benefit of priority from the Japanese Patent Application No. P2017-197100, filed Oct. 10, 2017 and the Japanese Patent Application No. P2018-189642, filed Oct. 5, 2018, the entire contents of all of which are incorporated herein by reference.

FIELD

Embodiments described herein relate generally to a medical imaging diagnosis apparatus and a scan planning device.

BACKGROUND

An X-ray computed tomography apparatus includes a bed which moves a table top on which a subject is placed. In order to obtain an image with higher fineness, reduction in vibration of the table top at a time of insertion into a bore is required. This being the case, a novel two-stage sliding-type bed has been under development. This bed includes a mechanism which can independently slide a table top and a support frame which supports the table top, and has a configuration that the support frame moves forward to the gantry in interlock with lifting of the table top. By this configuration, the support frame can be moved as close as possible to the gantry with a high throughput, and the reduction of vibration of the table top can be realized. On the other hand, there is a demand for vertical lifting of the table top relative to the floor surface.

BRIEF DESCRIPTION OF THE DRAWING

FIG. 8 is a view illustrating an example of an operation terminal according to the embodiment;

FIG. 9 is a view illustrating another example of the operation terminal according to the embodiment;

FIG. 10 is a view illustrating a configuration of an X-ray computed tomography system according to a modification of the embodiment.

DETAILED DESCRIPTION

In general, according to one embodiment, a medical imaging diagnosis apparatus includes a gantry, a bed and processing circuitry. The gantry is configured to acquire data. The bed is configured to support a table top such that the table top is horizontally and vertically movable relative to a floor surface. The processing circuitry is configured to determine a lift route of the table top from an initial height to a target height to be either a first route in which the table top is vertically lifted relative to the floor surface from the initial height to the target height, or a second route in which the table top is lifted, while being horizontally moved, relative to the floor surface from the initial height to the target height.

Hereinafter, an a medical imaging diagnosis apparatus and a scan planning device according to the embodiment will be described with reference to the accompanying drawings.

Figure 1:
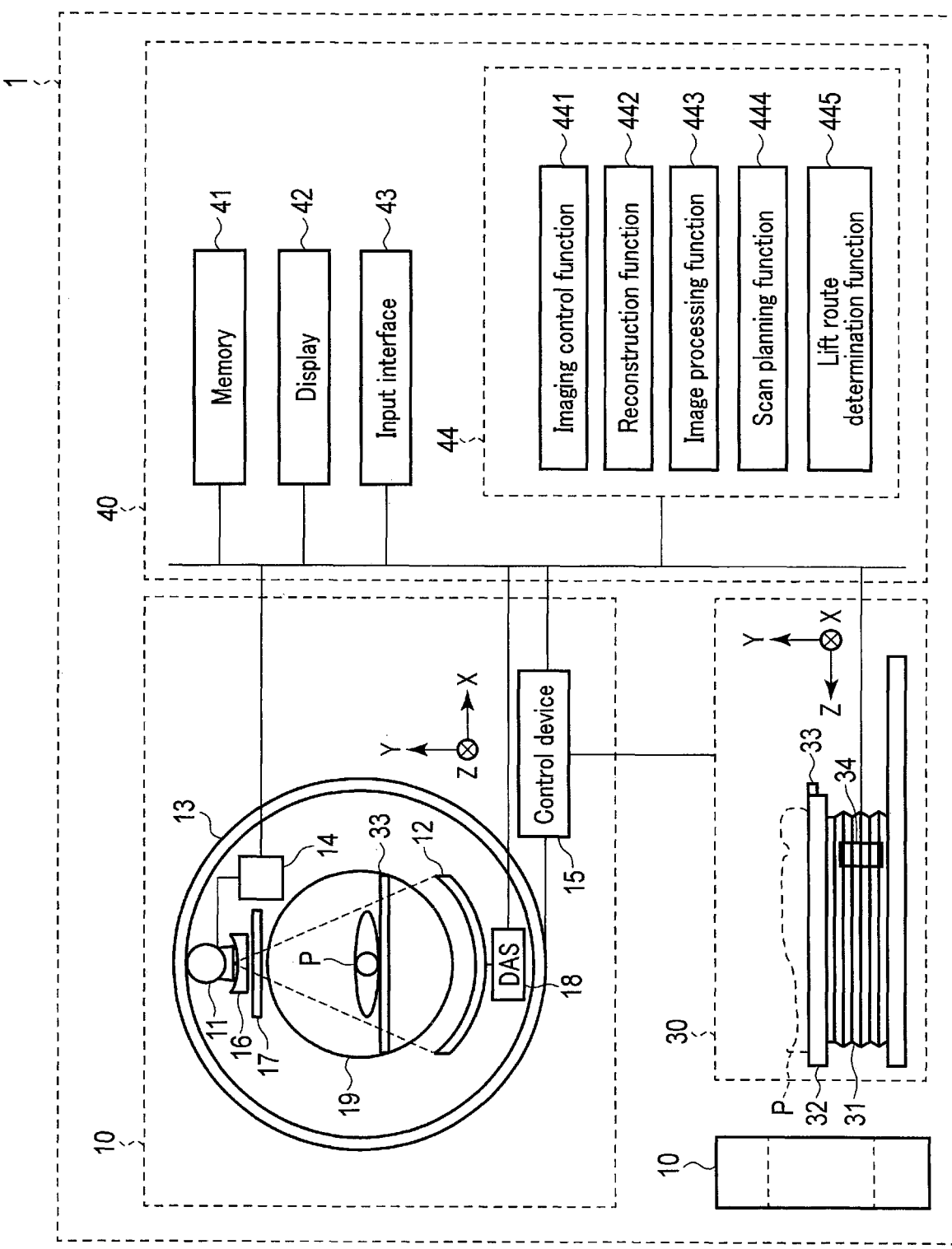
FIG. 1 is a view illustrating a configuration of an X-ray computed tomography apparatus according to an embodiment.

FIG. 1 is a view illustrating a configuration of an X-ray computed tomography apparatus 1 according to the embodiment. In the X-ray computed tomography apparatus 1, X-rays are radiated on a subject P from an X-ray tube 11, and the radiated X-rays are detected by an X-ray detector 12. Based on the output from the X-ray detector 12, the X-ray computed tomography apparatus 1 generates a CT image relating to the subject P.

As illustrated in FIG. 1, the X-ray computed tomography apparatus 1 includes a gantry 10, a bed 30 and a console 40. The gantry 10 is a scan device including a configuration for X-ray CT scan of the subject P. The bed 30 is a convey device for placing thereon the subject P that is the target of X-ray CT scan and for aligning the subject P. The console 40 is a computer which controls the gantry 10. For example, the gantry 10 and bed 30 are installed in a CT examination room, and the console 40 is installed in a control room adjacent to the CT examination room. The gantry 10, bed 30 and console 40 are communicably connected by wire or by radio. Note that the console 40 may not necessarily be installed in the control room. For example, the console 40 may be installed in the same room as the gantry 10 and bed 30. Besides, the console 40 may be built in the gantry 10.

As illustrated in FIG. 1, the gantry 10 includes the X-ray tube 11, the X-ray detector 12, a rotating frame 13, an X-ray high voltage device 14, a control device 15, a wedge 16, a collimator 17, and data acquisition circuitry (DAS: Data Acquisition System) 18.

The X-ray tube 11 radiates X-rays on the subject P. Specifically, the X-ray tube 11 includes a cathode which generates thermions, an anode which receives the thermions flying from the cathode and generates X-rays, and a vacuum tube which holds the cathode and anode. The X-ray tube 11 is connected to the X-ray high voltage device 14 via a high-voltage cable. A tube voltage is applied between the cathode and anode by the X-ray high voltage device 14. By the application of the tube voltage, thermions fly from the cathode toward the anode. By the thermions flying from the cathode toward the anode, a tube current flows. By the application of high voltage and the supply of filament current from the X-ray high voltage device 14, thermions fly from the cathode toward the anode, and X-rays are generated by the thermions impinging on the anode.

The X-ray detector 12 detects X-rays which are radiated from the X-ray tube 11 and pass through the subject P, and outputs to the DAS 18 an electric signal corresponding to the dose of the detected X-rays. The X-ray detector 12 has a configuration in which a plurality of X-ray detection element arrays, each including a plurality of X-ray detection elements arranged in a channel direction, are arranged in a slice direction (row direction). The X-ray detector 12 is an indirect-conversion-type detector including a grid, a scintillator array and an optical sensor array. The scintillator outputs light of an amount corresponding to an incident X-ray amount. The grid includes an X-ray shield plate which is disposed on the X-ray incident surface side of the scintillator array, and absorbs scattered X-rays. The optical sensor array converts the light from the scintillator to an electric signal corresponding to the amount of light from the scintillator. For example, a photodiode is used as the optical sensor.

The rotating frame 13 is an annular frame which supports the X-ray tube 11 and X-ray detector 12 such that the X-ray tube 11 and X-ray detector 12 are rotatable around a rotational axis Z. Specifically, the rotating frame 13 supports the X-ray tube 11 and X-ray detector 12 such that the X-ray tube 11 and X-ray detector 12 are opposed to each other. The rotating frame 13 is supported on a stationary frame (not shown) such that the rotating frame 13 is rotatable around the rotational axis Z. The control device 15 causes the rotating frame 13 to rotate around the rotational axis Z by the control device 15, thereby rotating the X-ray tube 11 and X-ray detector 12 around the rotational axis Z. The rotating frame 13 rotates at a fixed angular velocity around the rotational axis Z by receiving driving force from a driving mechanism of the control device 15. A field of view (FOV) is set in a bore 19 of the rotating frame 13.

In the present embodiment, the rotational axis of the rotating frame 13 in a non-tilt state or the longitudinal direction of the table top 33 of the bed 30 is defined as a Z direction; a direction orthogonal to the Z direction and horizontal to the floor surface is defined as an X direction; and a direction orthogonal to the Z direction and perpendicular to the floor surface is defined as a Y direction.

The X-ray high voltage device 14 includes a high voltage generation device and an X-ray control device. The high voltage generation device includes electric circuitry such as a transformer and a rectifier, and generates a high voltage which is applied to the X-ray tube 11 and a filament current which is supplied to the X-ray tube 11. The X-ray control device controls the high voltage which is applied to the X-ray tube 11 and the filament current which is supplied to the X-ray tube 11. The high voltage generation device may adopt either a transformer method or an inverter method. The X-ray high voltage device 14 may be provided in the rotating frame 13 in the gantry 10, or may be provided in the stationary frame (not shown) in the gantry 10.

The wedge 16 adjusts the dose of X-rays which are radiated on the subject P. Specifically, the wedge 16 attenuates X-rays such that the dose of X-rays radiated on the subject P from the X-ray tube 11 may have a predetermined distribution. For example, as the wedge 16, a metal plate of aluminum or the like, such as a wedge filter or a bow-tie filter, is used.

The collimator 17 restricts the range of radiation of X-rays which have passed through the wedge 16. The collimator 17 slidably supports a plurality of lead plates which shield X-rays, and adjusts the form of a slit which is formed by the lead plates.

The DAS 18 reads out an electric signal corresponding to the dose of X-rays, which were detected by the X-ray detector 12, from the X-ray detector 12, amplifies the read electric signal, and integrates electric signals over a view period, thereby acquiring detection data having a digital value corresponding to the dose of X-rays over the view period. The detection data is called "projection data". The DAS 18 is realized by an ASIC (Application Specific Integrated Circuit) on which a circuitry element that can generate projection data is mounted. The projection data is transmitted to the console 40 via a non-contact data transmission device or the like.

The control device 15 controls the X-ray high voltage device 14 and DAS 18 in order to execute X-ray CT imaging in accordance with an imaging control function 441 by processing circuitry 44 of the console 40. The control device 15 controls a projector (not shown) for patient alignment, such as an external light projector or an internal projector, which is provided in the gantry 10. The control device 15 includes processing circuitry including a CPU (Central Processing Unit) or an MPU (Micro Processing Unit) or the like, and a driving device such as a motor and an actuator or the like. The processing circuitry includes, as hardware resources, a processor such as a CPU, and a memory such as a ROM (Read Only Memory) or RAM (Random Access Memory). In addition, the control device 15 may be realized by an ASIC, FPGA (Field Programmable Gate Array), another CPLD (Complex Programmable Logic Device), or an SPLD (Simple Programmable Logic Device).

The bed 30 includes a base 31, a support frame 32, the table top 33, and a bed driving device 34. The base 31 is installed on the floor surface. The base 31 is a structure which supports the support frame 32 such that the support frame 32 is movable in the vertical direction (Y direction) relative to the floor surface. The support frame 32 is a frame provided on an upper part of the base 31. The support frame 32 supports the table top 33 such that the table top 33 is slidable along the central axis Z. The table top 33 is a plate with flexibility, on which the subject P is placed.

The bed driving device 34 is housed in the bed 30. The bed driving device 34 is a motor or an actuator which generates driving force for moving the support frame 32 and table top 33 on which the subject P is placed. The bed driving device 34 operates in accordance with the control by the console 40, etc.

The console 40 includes a memory 41, a display 42, an input interface 43 and processing circuitry 44. Data communication between the memory 41, display 42, input interface 43 and processing circuitry 44 is executed via a bus (BUS).

The memory 41 is a storage device which stores various information, such as an HDD (Hard Disk Drive), an SSD (Solid State Drive) or an integrated circuit storage device. The memory 41 stores, for example, projection data and reconstruction image data. The memory 41 may be, aside from the HDD, SSD or the like, a portable storage medium such as a CD (Compact Disc), a DVD (Digital Versatile Disc), a flash memory or the like, or may be a drive unit which reads/writes various information from/to a semiconductor memory device or the like, such as a RAM (Random Access Memory). Besides, a storage area of the memory 41 may exist in the X-ray CT apparatus 1, or may exist in an external storage device connected over a network.

The display 42 displays various kinds of information. The display 42 outputs, for instance, a medical image (CT image) generated by the processing circuitry 44, and a GUI (Graphical User Interface) or the like for accepting various kinds of operations from an operator. As the display 42, for example, use can be made of, as needed, a liquid crystal display (LCD), a CRT (Cathode Ray Tube) display, an organic EL display (OELD: Organic Electro Luminescence Display), a plasma display, or some other discretionarily chosen display.

The input interface 43 accepts various kinds of input operations from the operator, converts the accepted input operations to electric signals, and outputs the electric signals to the processing circuitry 44. As the input interface 43, for example, use can be made of, as needed, a mouse, a keyboard, a trackball, a switch, a button, a joystick, a touchpad, a touch panel display, etc. Note that in the present embodiment, the input interface 43 is not limited to a device including a physical operation part, such as a mouse, a keyboard, a trackball, a switch, a button, a joystick, a touchpad, a touch panel display, etc. Examples of the input interface 43 include processing circuitry of an electric signal, which receives an electric signal corresponding to an input operation from an external input device, which is provided separately from the apparatus, and outputs the received electric signal to the processing circuitry 44.

The processing circuitry 44 controls the operation of the entirety of the X-ray computed tomography apparatus 1 in accordance with an electric signal of an input operation which is output from the input interface 43. For example, the processing circuitry 44 includes, as hardware resources, a processor such as a CPU, an MPU, a GPU (Graphics Processing Unit), etc., and a memory such as a ROM, a RAM, etc. The processing circuitry 44 executes an imaging control function 441, a reconstruction processing function 442, an image processing function 443, a scan planning function 444 and a lift route determination function 445, by the processor which executes a program developed on the memory. Note that the embodiment is not limited to the case in which the respective functions 441 to 445 are realized by single processing circuitry. Processing circuitry may be composed by combining a plurality of independent processors, and the respective processors may execute programs, thereby realizing the functions 441 to 445.

In the imaging control function 441, the processing circuitry 44 controls the X-ray high voltage device 14, control device 15 and DAS 18 in order to execute X-ray CT scan. The processing circuitry 44 controls the X-ray high voltage device 14, control device 15 and DAS 18 in accordance with a scan condition which is determined by the scan planning function 444.

In the reconstruction processing function 442, the processing circuitry 44 generates a CT image, based on projection data which is output from the DAS 18. Specifically, the processing circuitry 44 applies preprocesses, such as a logarithmic conversion process, an offset correction process, an inter-channel sensitivity correction process and bean hardening correction, to the projection data which is output from the DAS 18. In addition, the processing circuitry 44 applies a reconstruction process, which uses a filtered back projection method or an iterative approximation reconstruction method, to the preprocessed projection data, thereby generating a CT image.

In the image processing function 443, the processing circuitry 44 converts the CT image, which is generated by the reconstruction processing function 442, to a tomographic image of an arbitrary cross section or a three-dimensional image, based on an input operation which was accepted from the operator via the input interface 43.

In the scan planning function 444, the processing circuitry 44 creates a scan plan automatically or in accordance with an instruction from the operator, which is input via the input interface 43 or the like. The scan plan includes a scan condition and a lift route. The lift route is a lift route of the table top 33 from an initial height to a target height, as will be described later in detail.

In the lift route determination function 445, the processing circuitry 44 determines the lift route, based on the scan condition, automatically or in accordance with an instruction from the operator, which is input via the input interface 43 or the like.

Figure 2:
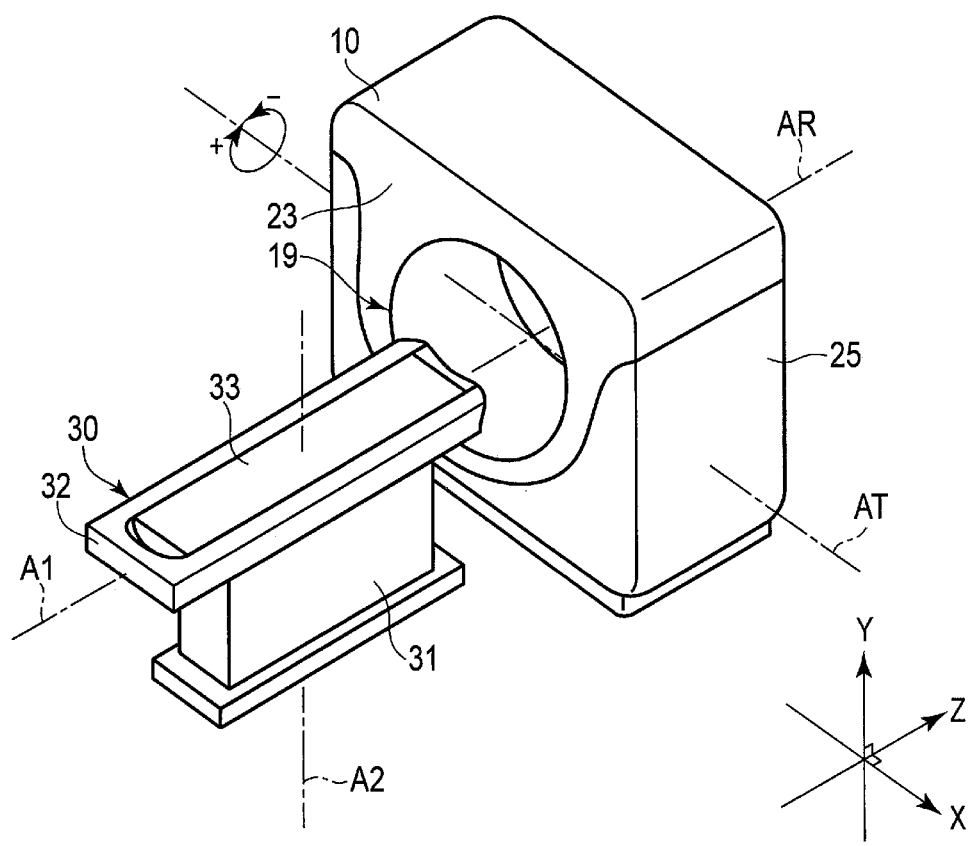
FIG. 2 is a perspective view illustrating an external appearance of a gantry according to the embodiment.

FIG. 2 is a perspective view illustrating the external appearance of the gantry 10 according to this embodiment. As illustrated in FIG. 2, the gantry 10 includes a gantry main body 23 in which the bore 19 with a substantially cylindrical shape is formed. The gantry main body 23 is supported by a stationary portion 25 installed on the floor surface, such that the gantry main body 23 is tiltable about a tilt axis AT. The tilt axis AT horizontally intersects at right angles with a central axis (rotational axis) AR of the bore 19. The bed 30 is installed in front of the gantry 10. The bed 30 is a two-stage sliding-type bed equipped with the base 31, support frame 32 and table top 33. As illustrated in FIG. 2, the bed 30 is disposed such that a long axis A1 of the table top 33 is parallel to a central axis AR of the bore 19.

The table top 33 is a plate-like structure having flexibility. The support frame 32 supports the table top 33 such that the table top 33 is slidable along the long axis A1. The base 31 supports the support frame 32 such that the support frame 32 is slidable along an axis parallel to the long axis A1 and can move up and down along a vertical axis A2 vertically crossing at right angles with the long axis A1. The vertical axis A2 is vertical to the floor surface. Hereinafter, a direction parallel to the long axis A1 of the table top 33 is referred to as "long direction" or "Z direction", and a direction parallel to the vertical axis A2 is defined as "vertical direction" or "Y direction". Furthermore, a direction in which the bed 30 approaches the gantry 10 is defined as "+Z direction", a direction in which the bed 30 moves away from the gantry 10 is defined as "−Z direction," a direction in which the bed 30 moves up is defined as "+Y direction," and a direction in which the bed 30 moves down is defined as the "−Y direction."

Figure 3:
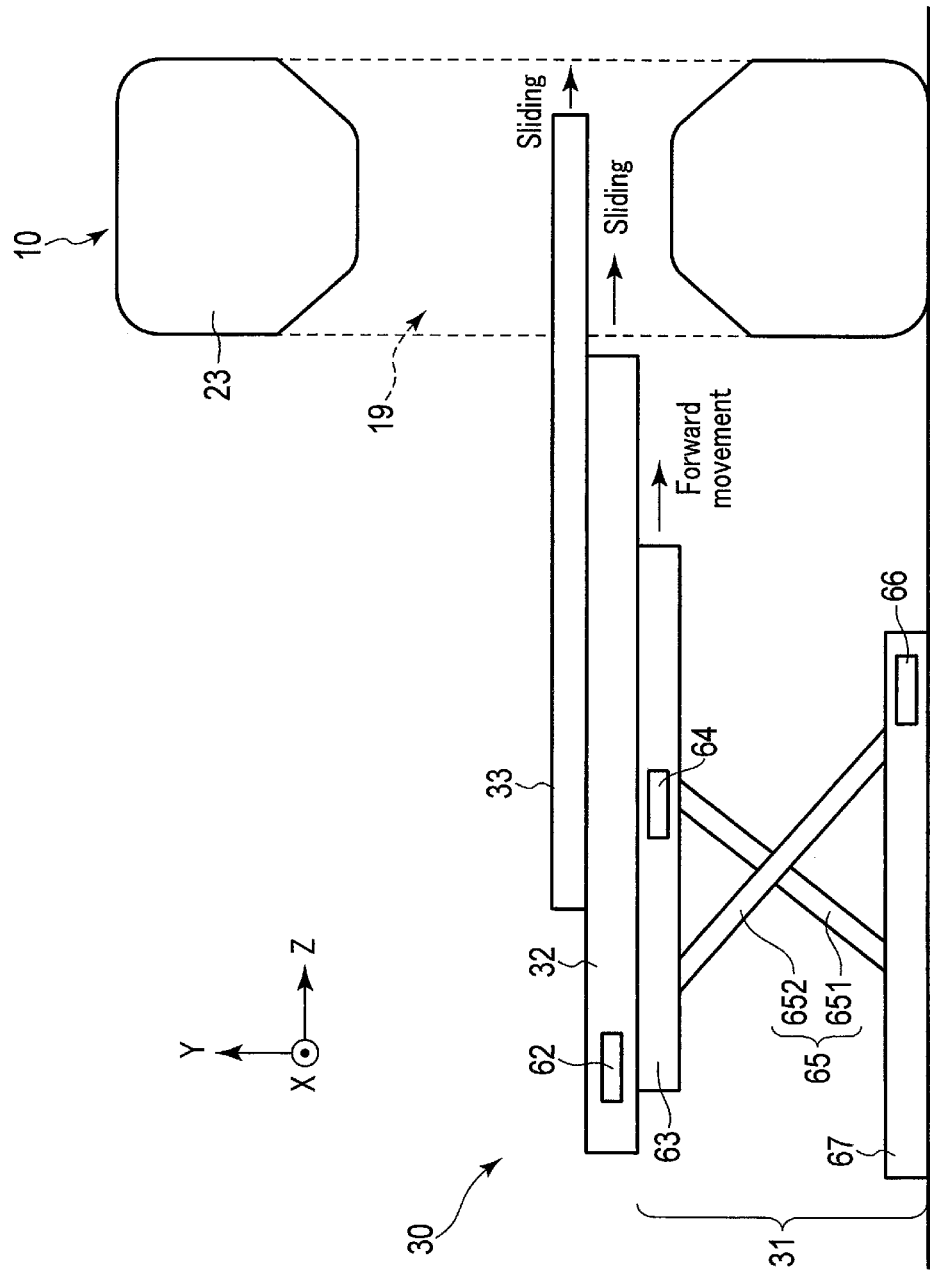
FIG. 3 is a view schematically illustrating a side surface of a bed according to the embodiment.

FIG. 3 is a view schematically illustrating a side surface of the bed 30 according to the present embodiment. Note that in FIG. 3, an illustration of the housing of the bed 30 is omitted. As illustrated in FIG. 3, the table top 33 is supported by the support frame 32 so as to be slidable in the Z direction parallel to the long direction of the table top 33. The support frame 32 may have any structure if the support frame 32 allows the table top 33 to slide. For example, the support frame 32 has a frame-like frame (not shown) that guides the sliding of the table top 33 in the Z direction. The support frame 32 is provided with a table top driving controller 62 that generates driving force for making the table top 33 slide in the Z direction. The table top driving controller 62 is realized by an existing motor such as a servo motor. The table top driving controller 62 operates under the control of the control device 15.

As illustrated in FIG. 3, the base 31 is installed on the floor surface. The base 31 moves up and down the support frame 32 in the Y direction, and moves forward and backward the support frame 32 in the Z direction. Specifically, the base 31 includes a stationary frame 63, an X link 65 and a mount 67. The stationary frame 63 supports the support frame 32 such that the support frame 32 is slidable in the Z direction which is parallel to the long direction of the support frame 32. The stationary frame 63 may have any structure if the stationary frame 63 allows the support frame 32 to slide. For example, the stationary frame 63 includes a frame-shaped frame which guides sliding of the support frame 32 in the Z direction. The stationary frame 63 is provided with a frame driving controller 64 that generates driving force for making the support frame 32 slide in the Z direction. The frame driving controller 64 is realized by an existing motor such as a servo motor. The frame driving controller 64 operates under the control of the control device 15.

As illustrated in FIG. 3, the base 31 includes a support structure which can move the stationary frame 63 up or down in the Y direction while moving the stationary frame 63 toward or away from the gantry 10. The X link 65 is connected to the stationary frame 63 and mount 67. The mount 67 is provided with a lift/lower driving controller 66 which generates driving force for causing the X link 65 to lift or lower the stationary frame 63 in the Y direction. The lift/lower driving controller 66 is realized by an existing motor such as a servo motor. The lift/lower driving controller 66 operates under the control of the control device 15.

As illustrated in FIG. 3, the X link 65 includes a pair of a movable link 651 and a fixed link 652 that are pivotally supported in an X form. The movable link 651 and the fixed link 652 are provided to be rotatable about a pivot shaft. The movable link 651 and the fixed link 652 are formed of, for example, a pair of metal plates having plate-like shapes and substantially the same length. One end of the fixed link 652 is fixed to the mount 67. The other end of the fixed link 652 is fixed to the stationary frame 63. One end of the movable link 651 is supported on the mount 67 so as to be slidable in the Z direction. The other end of the movable link 651 is supported on the stationary frame 63 so as to be slidable in the Z direction. The lift/lower driving controller 66 reduces the interval between the movable link 651 and the fixed link 652 in the Z direction, and thereby the stationary frame 63 approaches the gantry 10 while being lifted. The lift/lower driving controller 66 increases the interval between the movable link 651 and the fixed link 652 in the Z direction, and thereby the stationary frame 63 moves away from the gantry 10 while being lowered.

Figure 4:
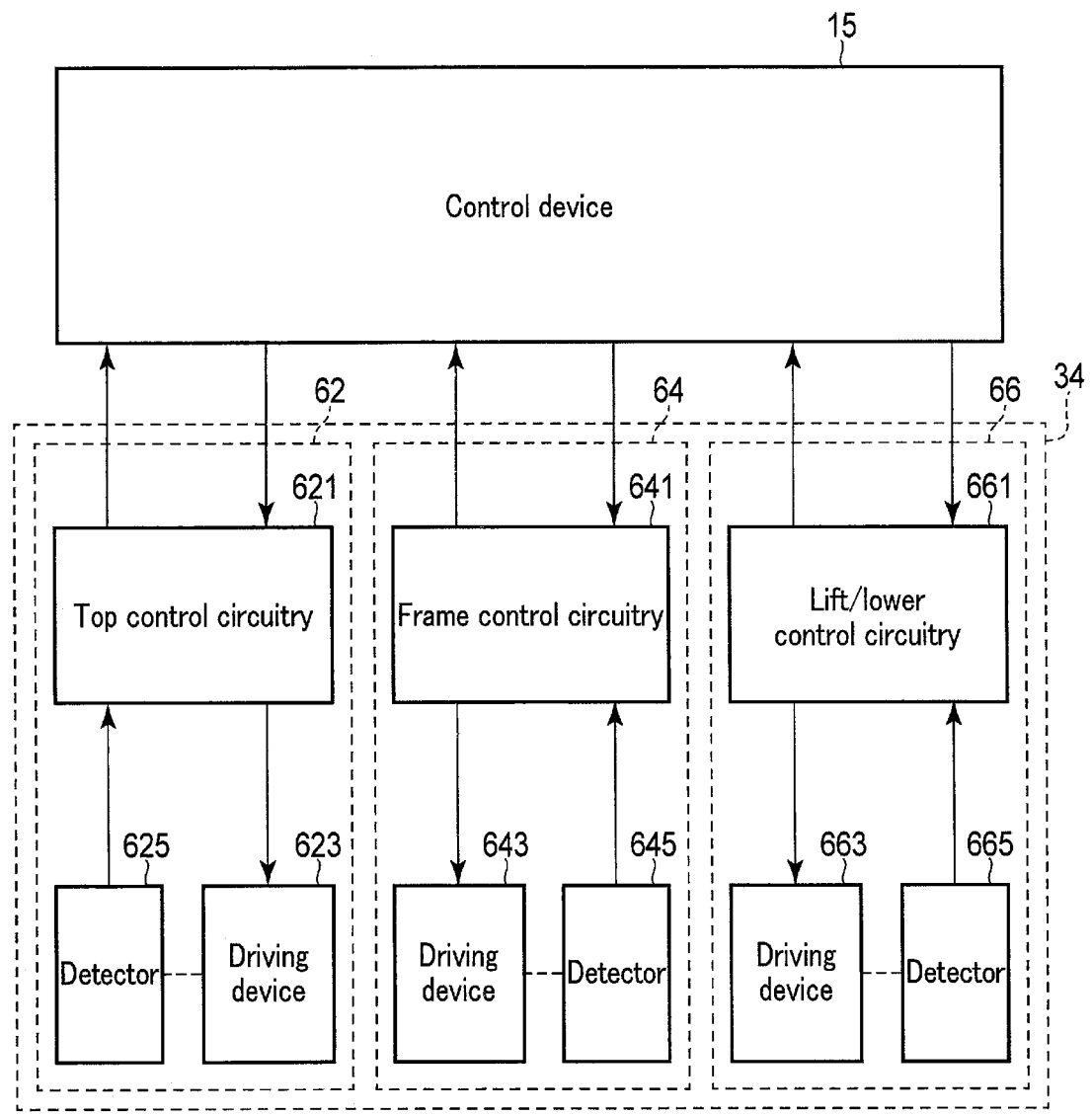
FIG. 4 is a view illustrating a configuration example of gantry control circuitry and a bed driving system according to the embodiment.

FIG. 4 is a view illustrating a configuration example of the control device 15 and bed driving device 34 according to this embodiment. As illustrated in FIG. 4, the bed driving device 25 includes the table top driving controller 62, frame driving controller 64, and lift/lower driving controller 66. The control device 15 controls the table top driving controller 62, frame driving controller 64 and lift/lower driving controller 66 to move the table top 33 to a desired position.

The table top driving controller 62 is provided on, for example, the support frame 32. The table top driving controller 62 causes the table top 33 to slide upon receiving an operation instruction signal from the control device 15. Specifically, the table top driving controller 62 includes table top control circuitry 621, a driving device 623, and a detector 625. The table top control circuitry 621 is a servo amplifier that receives an operation instruction signal from the control device 15 and supplies power corresponding to the operation instruction signal to the driving device 623. By receiving the power from the table top control circuitry 621, the driving device 623 is driven to actuate the support frame 32 to which the driving device 623 is connected, and to cause the table top 33 to slide. Specifically, the driving device 623 is a motor that generates driving force by rotating the drive shaft. The detector 625 is a position detector such as a rotary encoder provided on the drive shaft of the driving device 623.

The frame driving controller 64 is provided on, for example, the stationary frame 63. Upon receiving an operation instruction signal from the control device 15, the frame driving controller 64 causes the support frame 32 to slide. Specifically, the frame driving controller 64 includes frame control circuitry 641, a driving device 643, and a detector 645. The frame control circuitry 641 is a servo amplifier that receives an operation instruction signal from the control device 15 and supplies power corresponding to the operation instruction signal to the driving device 643. By receiving the power from the frame control circuitry 641, the driving device 643 is driven to actuate the stationary frame 64 to which the driving device 643 is connected, and to cause the support frame 32 to slide. Specifically, the driving device 643 is a motor that generates driving force by rotating the drive shaft. The detector 645 is a position detector such as a rotary encoder provided on the drive shaft of the driving device 643.

The lift/lower driving controller 66 is provided on, for example, the base 31. Upon receiving an operation instruction signal from the control device 15, the lift/lower driving controller 66 actuates the X link 65 to lift/lower (move up and down) the table top 33, support frame 32 and stationary frame 63. Specifically, the lift/lower driving controller 66 includes lift/lower control circuitry 661, a driving device 663, and a detector 665. The lift/lower control circuitry 661 is a servo amplifier that receives an operation instruction signal from the control device 15 and supplies power corresponding to the operation instruction signal to the driving device 663. By receiving the power from the lift/lower control circuitry 661, the driving device 663 is driven to actuate the X link 65, to which the driving device 663 is connected, and to lift/lower the table top 33, support frame 32 and stationary frame 63. The detector 665 is a position detector such as a rotary encoder provided on the drive shaft of the driving device 663.

Next, the operation of the X-ray computed tomography apparatus according to this embodiment will be described in detail.

As described above, in the lift route determination function 445, the processing circuitry 44 determines the lift route of the table top 33 from the initial height to target height. The lift route in this embodiment is generally classified into a vertical route and a non-vertical route.

Figure 5:
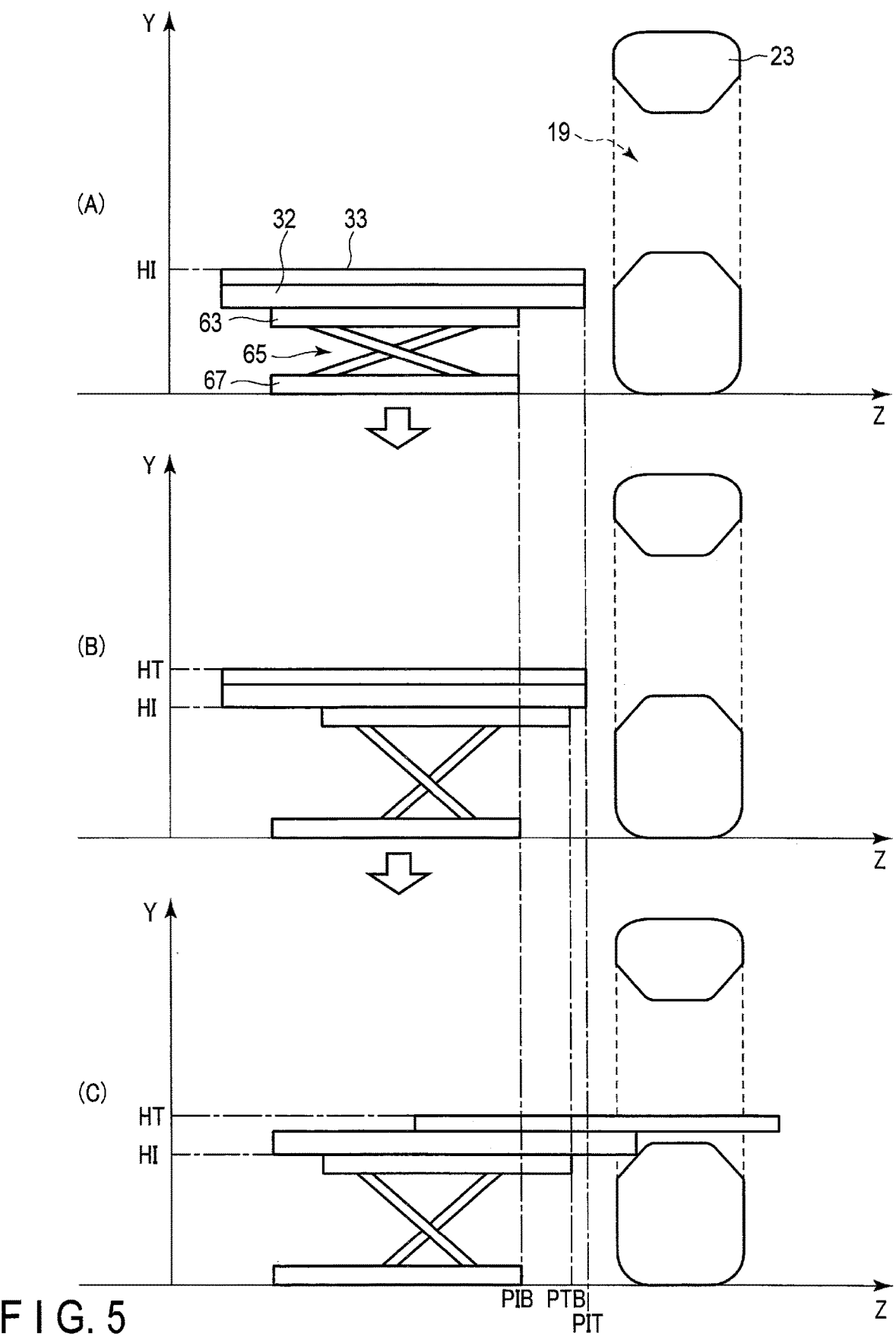
FIG. 5 is a view illustrating a movement of the bed with respect to a vertical route according the embodiment.

FIG. 5 is a view illustrating a movement of the bed 30 with respect to the vertical route. Part (A) of FIG. 5 is a view illustrating an external appearance of the bed 30 at a time when the table top 33 is at an initial height HI. Part (B) of FIG. 5 is a view illustrating an external appearance of the bed 30 at a time when the table top 33 is at a target height HT. Part (C) of FIG. 5 is a view illustrating an external appearance of the bed 30 at a time when the table top 33 is at the target height HT and the table top 33 is inserted into the bore 19. Note that in FIG. 5, an illustration of the housing of the bed 30 is omitted.

As illustrated in part (A) of FIG. 5, at an examination start time, the table top 33 is disposed at the initial height HI. The examination start time is set at, for example, a timing when a confirmation button has been pressed in a scan plan. The height of the table top 33 is defined as a height of a reference point of the table top 33 from the floor surface. Although the reference point may be set at an arbitrary portion of the table top 33, the reference point is, in FIG. 5, set at a subject placement surface of the table top 33. In addition, the position of the table top 33 in the Z direction is set as the position of a reference point of the table top 33 in the Z direction. Although this reference point may be set at an arbitrary portion of the table top 33, the reference point is, in FIG. 5, set at a distal end position of the table top 33 in the +Z direction.

As illustrated in part (B) of FIG. 5, the table top 33 is lifted by the X link 65 from the initial height HI to the target height HT. The target height HT is set to a height at which the table top 33 can be inserted into the bore 19. In interlock with the lift of the table top 33 by the X link 65, the stationary frame 63 moves forward in the +Z direction. For example, when the stationary frame 63 at the initial height HI is located at an initial horizontal position PIB, the stationary frame 63 at the target height HT moves forward to a position PTB which is closer to the gantry 10 than the initial horizontal position PIB. In the vertical route, in order to cancel the forward movement of the table top 33 and support frame 32 due to the forward movement of the stationary frame 63, the support frame 32 is slid in the −Z direction. Thereby, the horizontal position of the table top 33 and support frame 32 does not change from an initial horizontal position PIT, and is fixed. Specifically, since the table top 33 and support frame 32 are lifted vertically to the floor surface, the horizontal position at the initial height HI and the horizontal position at the target height HT are unchanged at the position PIT.

As illustrated in part (C) of FIG. 5, if the table top 33 is lifted vertically to the floor surface up to the target height HT, the support frame 32 approaches the gantry main body 23, and the table top 33 is inserted into the bore 19. Then, a CT examination is performed according to the scan plan.

The non-vertical route is a route in which the table top 33 and support frame 32 are lifted relative to the floor surface, while the positions of the table top 33 and support frame 32 in the Z direction are being varied. An example of the non-vertical route is a forward-movement route.

Figure 6:
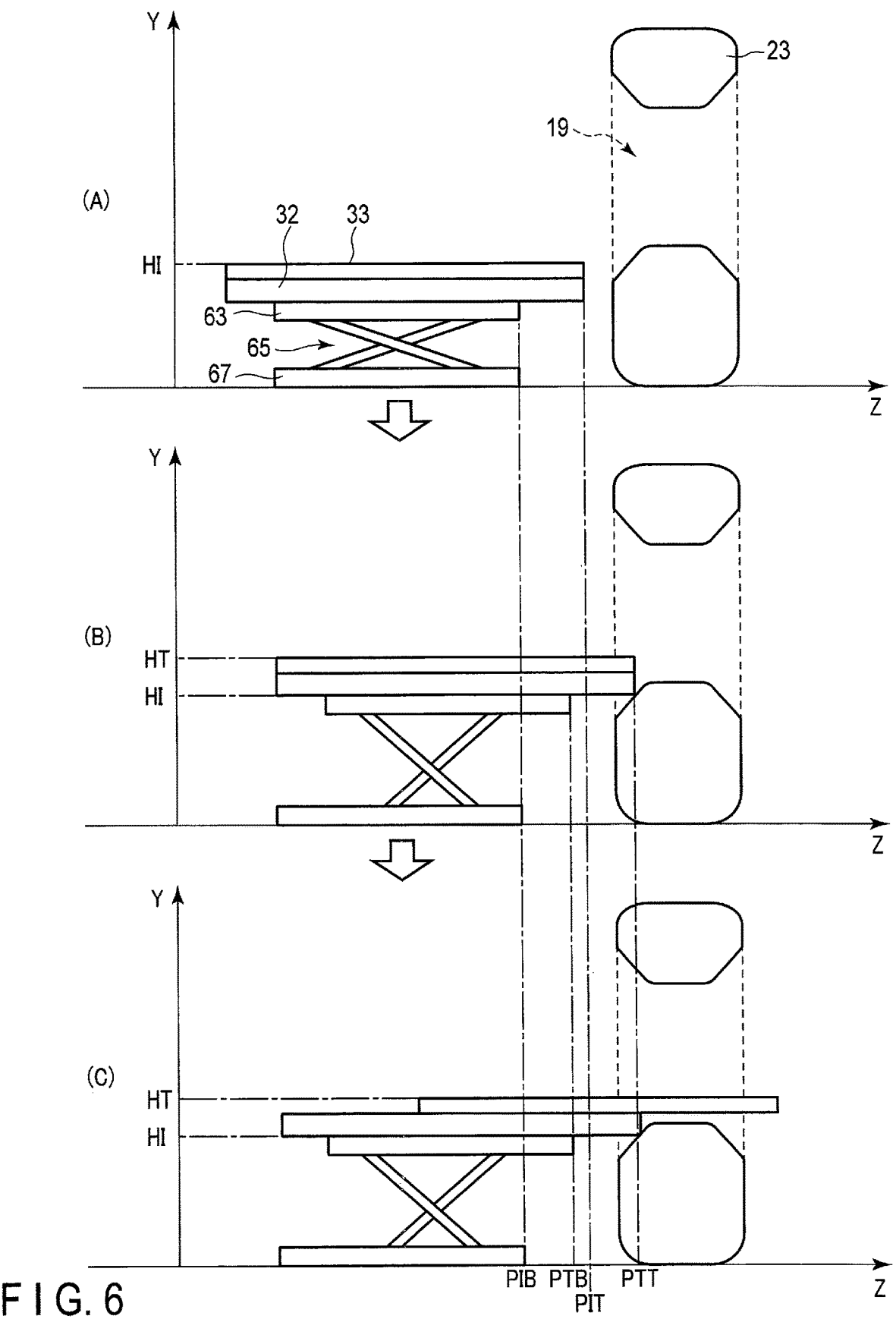
FIG. 6 is a view illustrating a movement of the bed with respect to a forward-movement route according to the embodiment.

FIG. 6 is a view illustrating a movement of the bed 30 with respect to the forward-movement route. Part (A) of FIG. 6 is a view illustrating an external appearance of the bed 30 at a time when the table top 33 is at the initial height HI. Part (B) of FIG. 6 is a view illustrating an external appearance of the bed 30 at a time when the table top 33 is at the target height HT. Part (C) of FIG. 6 is a view illustrating an external appearance of the bed 30 at a time when the table top 33 is at the target height HT and the table top 33 is inserted into the bore 19. Note that in FIG. 6, an illustration of the housing of the bed 30 is omitted.

As illustrated in part (B) of FIG. 6, the table top 33 is lifted by the X link 65 from the initial height HI to the target height HT. The target height HT is set to a height at which the table top 33 can be inserted into the bore 19. In interlock with the lift of the table top 33 by the X link 65, the stationary frame 63 moves forward in the +Z direction. For example, when the stationary frame 63 at the initial height HI is located at the initial horizontal position PIB, the stationary frame 65 at the target height HT moves forward to the position PTB which is closer to the gantry 10 than the initial horizontal position PIB. In the forward-movement route, the table top 33 and support frame 32 move forward in accordance with the forward movement of the stationary frame 63. For example, when the table top 33 and support frame 32 at the initial height HI are located at the initial horizontal position PIT, the table top 33 and support frame 32 at the target height HT move forward to a position PTT which is closer to the gantry 10 than the initial horizontal position PIT. The position PTT is set as a position where the support frame 32 does not collide with the gantry main body 23.

As illustrated in part (C) of FIG. 6, if the table top 33 is lifted to the target height HT, the table top 33 is inserted into the bore 19. Then, a CT examination is executed according to the scan plan. In the forward-movement route, the support frame 32 moves as close as possible to the gantry main body 23 while being lifted. Thus, the throughput of the CT examination is improved by the forward-movement route.

Figure 7:
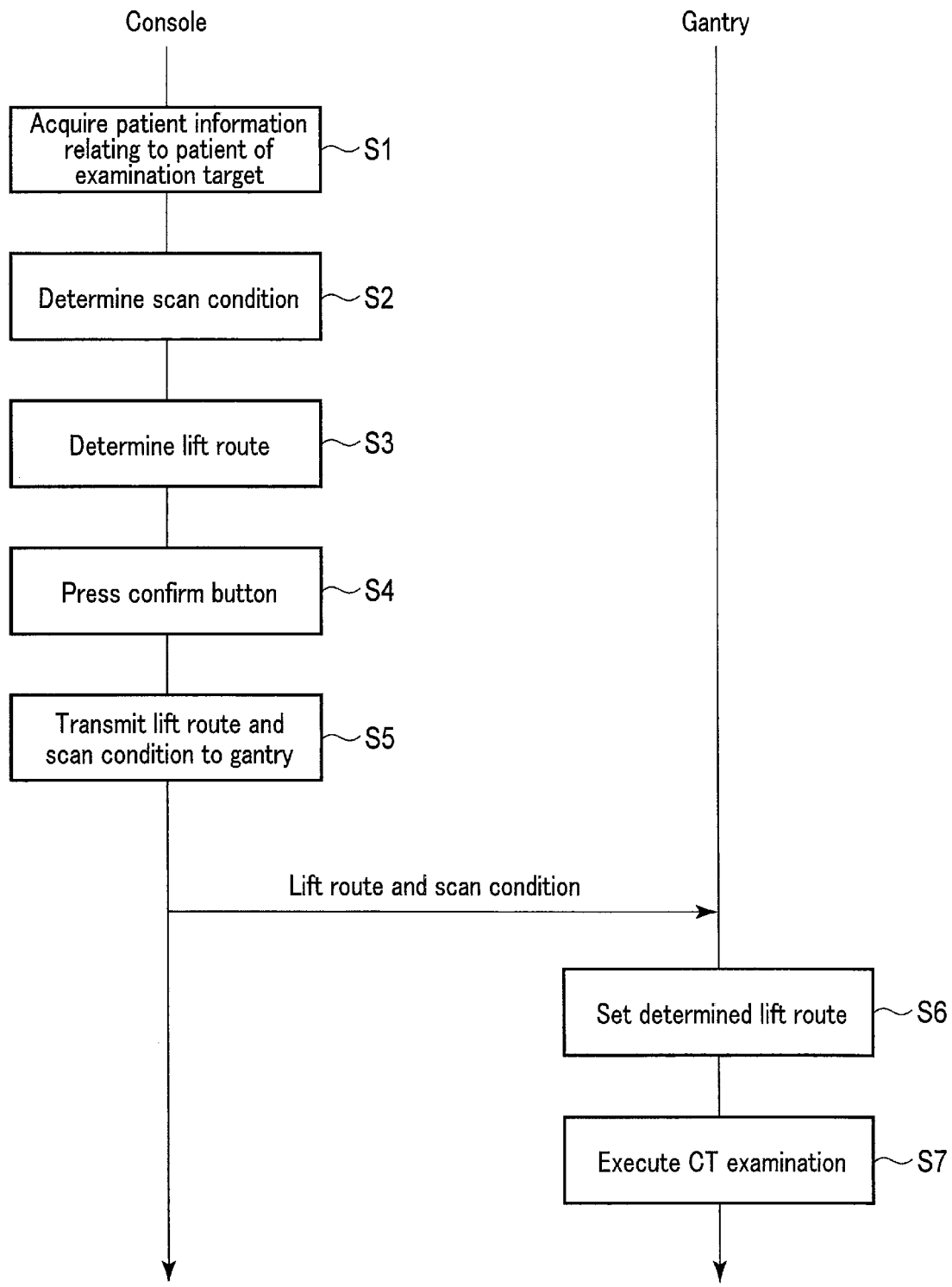
FIG. 7 is a view illustrating a typical flow of a CT examination by the X-ray computed tomography apparatus according to the embodiment.

Next, a flow of a CT examination by the X-ray computed tomography apparatus will be described. FIG. 7 is a view illustrating a typical flow of a CT examination by the X-ray computed tomography apparatus according to the present embodiment.

As illustrated in FIG. 7, the processing circuitry 44 of the console 40 first acquires patient information relating to a patient of an examination target (step S1). For example, the processing circuitry 44 acquires the patient information relating to the patient of the examination target from an RIS (Radiology Information System), a PACS (Picture Archiving and Communication System) or the like via a communication interface (not shown).

If step S1 is executed, the processing circuitry 44 executes the scan planning function 444 (step S2). In step S2, the processing circuitry 44 determines a scan condition. The scan condition includes an X-ray condition, a scan region, an FOV, etc. The scan condition in this embodiment also includes information of remarks, for example, the direction of the subject P on the table top 33, such as head-first, and the presence/absence of use of a stretcher. Each item of the scan condition is determined automatically or in accordance with an instruction of the operator via the input interface 43.

If step S2 is executed, the processing circuitry 44 executes the lift route determination function 445 (step S3). In step S3, the processing circuit 44 automatically determines the lift route, based on the scan condition. Hereinafter, the determination of the lift route, which is based on the scan condition, will be described by referring to a concrete example.

For example, when the scan region is the head, the vertical route is selected as the lift route. The reason is as follows. In the head scan, alignment is performed by an external light projector. As described above, in the case of the forward-movement route, the support frame 32 approaches the gantry main body 23 in accordance with the lift of the table top 33. Specifically, at a time point when the table top 33 is lifted up to the target height, the head has already moved to a position which is closer to a scan plane than to a projection line from the external light projector, and alignment using the external light projector is difficult. Thus, when the scan region is the head, the vertical route may better be selected as the lift route. When the scan region is a region other than the head, such as the chest region, abdominal region or lower limbs, alignment by the external light projector is not performed, or alignment by the external light projector can normally be performed. Thus, when the scan region is other than the head, the forward-movement route may better be selected as the lift route.

The processing circuitry 44 reads out the scan condition, and judges whether the parameter of the scan region of the scan condition is the head or not. When the processing circuitry 44 judges that the parameter of the scan region is the head, the processing circuitry 44 selects the vertical route as the lift route. When the processing circuitry 44 judges that the parameter of the scan region is not the head, the processing circuitry 44 selects the forward-movement route as the lift route.

Note that the judgment as to whether the scan region is the head or not may not be executed based on the parameter of the scan region. For example, the processing circuitry 44 may estimate that the scan region is the head, based on the information registered in a remarks column of the scan condition, which is included in a scan plan screen. Specifically, when text information of head-first is included in the remarks column, the processing circuitry 44 estimates that the scan region is the head. The head-first indicates the direction of the subject on the table top 33, and indicates that the head of the patient is located in the +Z direction.

Specifically, when the text information of head-first is included in the remarks column, the processing circuitry 44 selects the vertical route as the lift route.

In addition, when text information indicative of the alignment by the external light projector is included in the remarks column of the scan plan screen, the processing circuitry 44 may select the vertical route as the lift route.

The processing circuitry 44 may automatically determine the lift route, based on patient information. To be more specific, the processing circuitry 44 determines the lift route, based on the scan condition of the previous examination relating to the patient of the examination target. Concretely, the processing circuitry 44 first judges whether the scan condition of the previous examination relating to the patient of the examination target exists in the patient information relating to the patient of the examination target, which was acquired in step S1. When the scan condition of the previous examination exists, the processing circuitry 44 judges whether the scan region in the scan condition of the previous examination is the head or not. When the scan region of the previous examination is the head, the processing circuitry 44 estimates that the scan region of the present examination is also the head, and selects the vertical route as the lift route of the present examination. When the scan region of the previous examination is not the head, the processing circuitry 44 estimates that the scan region of the present examination is not the head either, and selects the forward-movement route as the lift route of the present examination.

On the other hand, when the processing circuitry 44 judges that the scan condition of the previous examination relating to the patient of the examination target does not exist, the processing circuitry 44 may determine the lift route, based on the scan condition of the present examination, as described above.

In this manner, when the processing circuitry 44 regards the scan condition of the previous examination and the scan condition of the present examination as being identical, and when the scan region of the previous examination is the head, the processing circuitry 44 selects the vertical route as the lift route of the present examination. On the other hand, when the scan region of the previous examination is not the head, the processing circuitry 44 selects the forward-movement route as the lift route of the present examination.

Besides, the processing circuitry 44 may determine the lift route of the present examination, based on the lift route of the previous examination. For example, the processing circuitry 44 may regard the lift route of the previous examination and the lift route of the present examination as being identical, and may select the same lift route as the lift route of the previous examination, as the lift route of the present examination. Specifically, when the lift route of the previous examination is the vertical route, the processing circuitry 44 selects the vertical route as the lift route of the present examination. When the lift route of the previous examination is the forward-movement route, the processing circuitry 44 selects the forward-movement route as the lift route of the present examination. The lift route of the previous examination is registered, for example, in the remarks column of the scan condition of the previous examination in the scan plan screen.

The processing circuitry 44 may determine the lift route by utilizing the information relating to the presence/absence of use of a stretcher, which is included in the remarks column of the scan condition. The stretcher is used for carrying the subject into the CT examination room. When the stretcher is used, the height of the stretcher from the floor surface is made equal to the height of the table top 33 from the floor surface, and then the subject is moved from the stretcher onto the table top 33 by healthcare workers or the like. In the case of the forward-movement route, since the position of the stretcher in the Z direction has to be also adjusted, the positioning between the stretcher and table top 33 becomes complex. Thus, when the stretcher is used, the vertical route may better be selected as the lift route. Specifically, when text information indicative of the use of a stretcher is included in the remarks column of the scan condition, the processing circuitry 44 selects the vertical route as the lift route. When the text information indicative of the use of the stretcher is not included in the remarks column of the scan condition, the processing circuitry 44 selects the forward-movement route as the lift route.

If step S3 is executed, the processing circuitry 44 displays on the display 42 the scan condition determined in step S2 and the lift route determined in step S3. The scan condition and lift route are displayed, for example, on the scan plan screen. In addition, the processing circuitry 44 displays a confirm button on the scan plan screen, and stands by for the pressing of the confirm button. The confirm button is a button for confirming the scan condition determined in step S2 and the lift route determined in step S3. The operator presses the confirm button via the input device or the like, when the operator has judged that there is no problem even if a CT examination is performed with the scan condition determined in step S2 and the lift route determined in step S3.

If the confirm button is pressed (step S4), the processing circuitry 44 transmits to the gantry 10 the lift route determined in step S3 and the scan condition determined in step S2 (step S5).

Note that a part on which the scan condition and lift route are displayed is not limited to the display 42 provided on the console 40, if the scan condition and lift route can be visually recognized by the operator. For example, the scan condition and lift route may be displayed on a display or an operation panel provided on the gantry 10.

If step S5 is executed, the control device 15 of the gantry 10 sets, as the operation mode of the bed 30, the lift route which was transmitted in step S5 (step S6). Concretely, when the vertical route was selected in step S3, the control device 15 sets the operation mode of the bed 30 to the vertical route. When the forward-movement route was selected in step S3, the control device 15 sets the operation mode of the bed 30 to the forward-movement route.

If step S6 is executed, the control device 15 executes a series of CT examinations, such as a patient alignment, an alignment scan and a main scan, in accordance with the scan condition (step S7). In the patient alignment, etc., when the control device 15 lifts the table top 33 from the initial height to the target height, the control device 15 lifts the table top 33 in accordance with the lift route which was set in step S6. Specifically, when the vertical route was set, the control device 15 controls the table top driving controller 62, frame driving controller 64 and lift/lower driving controller 66, as illustrated in FIG. 5, and the control device 15 lifts the table top 33 from the initial height to the target height and slides the support frame 32 in the −Z direction in order to cancel the forward movement of the support frame 32 in the +Z direction. Thereby, the table top 33 can be vertically lifted up to the target height. Thereafter, the subject is aligned by utilizing the external light projector or the like. After the subject is aligned, the control device 15 controls the table top driving controller 62 and frame driving controller 64 in accordance with the operator's instruction via the input device or the like, and inserts the table top 33 into the bore 19 such that the scan region crosses the scan plane, while moving the support frame 32 closer to the gantry main body 23.

When the forward-movement route was set, the control device 15 controls the lift/lower driving controller 66, as illustrated in FIG. 6, and lifts the table top 33 from the initial height to the target height, while moving forward the support frame 32 in the +Z direction. Thereby, with a high throughput, the table top 33 can be inserted into the bore 19 while the support frame 32 is moved as close as possible to the gantry main body 23. Thereafter, the subject is aligned by utilizing the external light projector or the like. The control device 15 controls the table top driving controller 62 and frame driving controller 64 in accordance with the operator's instruction via the input device or the like, and inserts the table top 33 into the bore 19 such that the scan region crosses the scan plane, while moving the support frame 32 closer to the gantry main body 23.

By the above, the flow of the CT examination by the X-ray computed tomography apparatus according to the present embodiment has been described. Note that the flow of the process illustrated in FIG. 7 is merely an example, and the embodiment is not limited to this example. For example, the scan planning in step S2, the determination of the lift route in step S3 and the pressing of the confirm button in step S4 may be executed by the control device 15 or the like of the gantry 10. In this case, the patient information acquired by the console 40 in step S1 is delivered from the console 40 to the gantry 10.

In the above description, it is assumed that the lift route is automatically determined based on the scan condition, etc. However, the present embodiment is not limited to this. The lift route may be manually determined via an operation terminal or the like. This operation terminal may be provided on the gantry 10, or may be provided on the bed 30 or console 40. In addition, this operation terminal may be a wireless terminal or the like, which can communicate with the gantry 10. Note that, in embodiments to be described below, it is assumed that the operation terminal is provided on the gantry 10.

FIG. 8 is a view illustrating an example of an operation terminal 431. As illustrated in FIG. 8, the operation terminal 431 includes, for example, a vertical lift button B1, a forward-movement lift button B2, a slide+ button B3 for the table top 33, a slide− button B4 for the table top 33, a slide+ button B5 for the support frame 32, a slide− button B6 for the support frame 32, and an a lowering button B7. The buttons B1 to B7 may be software buttons displayed on an operation panel, or may be hardware buttons.

The vertical lift button B1 is a button for lifting the table top 33 in the vertical route. While the vertical lift button B1 is being pressed, the control device 15 controls the table top driving controller 62, frame driving controller 64 and lift/lower driving controller 66, and the control device 15 lifts the table top 33 and slides the support frame 32 in the −Z direction in order to cancel the forward movement of the support frame 32 in the +Z direction.

The forward-movement lift button B2 is a button for lifting the table top 33 in the forward-movement route. While the forward-movement lift button B2 is being pressed, the control device 15 controls the lift/lower driving controller 66, and lifts the table top 33 while moving forward the support frame 32 in the +Z direction.

The slide+ button B3 is a button for sliding the table top 33 in the +Z direction, relative to the support frame 32. While the slide+ button B3 is being pressed, the control device 15 controls the table top driving controller 62 and slides the table top 33 in the +Z direction, relative to the support frame 32.

The slide− button B4 is a button for sliding the table top 33 in the −Z direction, relative to the support frame 32. While the slide− button B4 is being pressed, the control device 15 controls the table top driving controller 62 and slides the table top 33 in the −Z direction, relative to the support frame 32.

The slide+ button B5 is a button for sliding the support frame 32 in the +Z direction, relative to the stationary frame 63. While the slide+ button B5 is being pressed, the control device 15 controls the frame driving controller 64 and slides the support frame 32 in the +Z direction, relative to the stationary frame 63.

The slide− button B6 is a button for sliding the support frame 32 in the −Z direction, relative to the stationary frame 63. While the slide− button B6 is being pressed, the control device 15 controls the frame driving controller 64 and slides the support frame 32 in the −Z direction, relative to the stationary frame 63.

The lowering button B7 is a button for lowering the table top 33. While the lowering button B7 is being pressed, the control device 15 controls the lift/lower driving controller 66 and lowers the table top 33.

When the operation terminal 431 is provided on the X-ray computed tomography apparatus, the lift route can be determined by a manual operation on the operation terminal 431. Thus, the automatic determination means of the lift route, which is based on the scan condition or the like as described above, is needless.

However, the X-ray computed tomography apparatus may be equipped with both the automatic determination means of the lift route and the manual determination means by the operation terminal 431. For example, even when the lift route is determined based on the scan condition, etc., as illustrated in FIG. 7, the table top 33 may be lifted in a different lift route by the operation of the operation terminal 431. Specifically, when the lift route selected via the operation terminal 431 is different from the already set lift route, the control device 15 preferentially applies the lift route selected via the operation terminal 431.

For example, even when the forward-movement route was automatically set by the processing circuitry 44 in step S3, if the operator judges that the vertical route is preferable, the operator presses the vertical lift button B1. When the vertical lift button B1 was pressed, the control device 15 switches the operation route from the forward-movement route to the vertical route. Then, while the vertical lift button B1 is being pressed, the control device 15 controls the table top driving controller 62, frame driving controller 64 and lift/lower driving controller 66, and the control device 15 lifts the table top 33 and slides the support frame 32 in the −Z direction in order to cancel the forward movement of the support frame 32 in the +Z direction. Conversely, even when the vertical route was automatically set by the processing circuitry 44 in step S3, if the operator judges that the forward-movement route is preferable, the operator presses the forward-movement lift button B2. When the forward-movement lift button B2 was pressed, the control device 15 switches the operation route from the vertical route to the forward-movement route. Then, while the forward-movement lift button B2 is being pressed, the control device 15 controls the lift/lower driving controller 66, and the control device 15 lifts the table top 33 while moving forward the support frame 32 in the +Z direction.

Note that the control device 15 displays the present lift route on, for example, the display provided on the gantry 10, so that the operator can easily confirm the present lift mode. In addition, the vertical lift button B1 and forward-movement lift button B2 may be provided with light sources. In this case, the control device 15 turns on the light source of the vertical lift button B1 or forward-movement lift button B2, which corresponds to the present lift mode. Thereby, the operator can confirm the present lift route and can execute the operation of the bend 30 by the operation terminal 431.

Besides, the above-described operation terminal 431 is merely an example, and the present embodiment is not limited to this. For example, the operation terminal 431 may include a button for automatically evacuating the table top 33 to the initial position, a button for automatically moving the table top 33 to a predetermined position in the bore 19, and operation buttons of the external light projector and internal projector. In addition, other buttons relating to the lift route may be provided.

FIG. 9 is a view illustrating another operation terminal 432. As illustrated in FIG. 9, the operation terminal 432 includes a vertical route button B8, a forward-movement button B9 and a lift button B10, instead of the vertical lift button B1 and forward-movement lift button B2 of the operation terminal 431 of FIG. 8.

The vertical route button B8 is a button for selecting the vertical route as the lift route. When the vertical route button B8 was pressed, the control device 15 sets the lift route to the vertical route. The vertical route button B8 is provided with a light source. When the vertical route was set, the control device 15 turns on the light source of the vertical route button B8.

The forward-movement route button B9 is a button for selecting the forward-movement route as the lift route. When the forward-movement route button B9 was pressed, the control device 15 sets the lift route to the forward-movement route. The forward-movement route button B9 is provided with a light source. When the forward-movement route was set, the control device 15 turns on the light source of the forward-movement route button B9.

The lift button B10 is a button for lifting the table top 33 in accordance with the lift route which was set by the pressing of the vertical route button B8 or forward-movement route button B9. While the lift button B10 is being pressed, the control device 15 executes control for lifting the table top 33 in accordance with the set lift route. Specifically, when the vertical route was set, the control device 15 controls the table top driving controller 62, frame driving controller 64 and lift/lower driving controller 66, and the control device 15 lifts the table top 33 and slides the support frame 32 in the −Z direction in order to cancel the forward movement of the support frame 32 in the +Z direction. When the forward-movement route was set, the control device 15 controls the lift/lower driving controller 66, and the control device 15 lifts the table top 33 while moving forward the support frame 32 in the +Z direction.

The operation terminal 432 has been described as being equipped with two buttons, namely the vertical route button B8 and forward-movement route button B9, in order to select the vertical route or forward-movement route. However, the present embodiment is not limited to this. For example, the operation terminal 432 may be equipped with a single select button. In this case, each time the select button is pressed, the control device 15 switches the lift route between the vertical route and the forward-movement route.

The control device 15 may set a default lift route. In this case, responding to a notification that the subject P was changed, the control device 15 sets the lift route to the default lift route. The fact that the subject P was changed is recognized, for example, by the supply of a signal, which is indicative of the pressing of the confirm button, from the console 40 to the control device 15.

A combination of the vertical lift button B1 and forward-movement lift button B2, or a combination of the vertical route button B8, forward-movement route button B9 and lift button B10, may be mounted on a footswitch of the bed 30.

The determination of the lift route is not limited to the mode in which the lift route is automatically determined based on the scan condition, etc., or is manually determined via the operation terminal 431, 432. For example, the lift route may be switched in interlock with a power assist function provided in the bed 30. Specifically, based on the fact that a handle provided on the bed 30 is vertically pulled up by the operator or the like, the control device 15 sets the lift route to the vertical route, and immediately the control device 15 controls the table top driving controller 62, frame driving controller 64 and lift/lower driving controller 66, and the control device 15 lifts the table top 33 and slides the support frame 32 in the −Z direction in order to cancel the forward movement of the support frame 32 in the +Z direction. Thereby, the lift route can be set to the vertical route in interlock with the operation by the operator of vertically pulling up the bed 30 or table top 33.

As described above, the X-ray computed tomography apparatus 1 according to this embodiment includes the gantry 10, bed 30 and processing circuitry 44. The gantry 10 executes X-ray CT scan. The bed 30 supports the table top 33 such that the table top 33 is horizontally and vertically movable relative to the floor surface. The processing circuitry 44 determines the lift route of the table top 33 from the initial height to the target height to be either the vertical route in which the table top 33 is vertically lifted relative to the floor surface from the initial height to target height, or the non-vertical route in which the table top 33 is vertically lifted, while being horizontally moved, relative to the floor surface from the initial height to target height.

By the above configuration, the X-ray computed tomography apparatus 1 according to this embodiment can select one of the vertical route and the non-vertical route. Therefore, the flexibility relating to the selection of the lift route of the table top 33 can be improved.

Note that the above-described configuration of the bed 30 is merely an example, and the embodiment is not limited to this. For example, the bed 30 according to the embodiment may have any configuration if the table top 33 and the table top support structure, such as the support frame 32, can be vertically lifted and lowered relative to the floor surface and is independently horizontally movable in the Z direction. For example, instead of the support frame 32 and base 31, a self-advancing base may be provided which slidably supports the table top 33 and is independently horizontally movable in the Z direction.

Moreover, the base 31 of the bed 30 according to the embodiment has been described as being equipped with the X link 65 which moves the table top 33 and support frame 32 toward or away from the gantry 10 in accordance with lifting and lowering. However, the embodiment is not limited to this. The base 31 according to the embodiment may be equipped with any lift/lower mechanism if the table top 33 and support frame 32 can be lifted and lowered. For example, the base 31 may be equipped with an X link which lifts and lowers the table top 33 and support frame 32 while fixing the distance of the gantry 10 to the table top 33 and support frame 32, or may be equipped with a lift/lower mechanism other than an X link. In this configuration, for example, in the case of the vertical route, the control device 15 simply controls the lift/lower driving controller 66, and vertically lifts the table top 33 and support frame 32 relative to the floor surface via this lift/lower mechanism. In the forward-movement mode, while vertically lifting the table top 33 and support frame 32 relative to the floor surface via this lift/lower mechanism, the control device 15 controls the table top driving controller 62 to slide the table top 33 in the +Z direction into the bore 19 while controlling the frame driving controller 64 to slide the support frame 32 in the +Z direction toward the gantry main body 23. Thereby, even with a bed which does not adopt the forward-movement method as in this embodiment, one of a plurality of lift routes can discretionarily be selected.

Besides, in the present embodiment, the medical imaging diagnosis apparatus equipped with the bed 30 has been described as being the X-ray computed tomography apparatus. However, the embodiment is not limited to this. The medical imaging diagnosis apparatus may be any kind of medical imaging diagnosis apparatus, if the medical imaging diagnosis apparatus includes the gantry in which an imaging mechanism that acquires medical data relating to a subject is mounted. For example, the medical imaging diagnosis apparatus according to the embodiment may be, aside from the X-ray computed tomography apparatus, a magnetic resonance imaging apparatus, a SPECT (single photon emission CT) apparatus, a PET (positron emission tomography) apparatus, or an X-ray diagnostic apparatus (X-ray angiography apparatus). In the case of the magnetic resonance imaging apparatus, the gantry includes, for example, a static field magnet, a gradient coil and a transmitter/receiver coil. In the case of the SPECT apparatus and PET apparatus, the gantry includes a gamma ray detector. In the case of the X-ray diagnostic apparatus, the gantry is an arm in which an X-ray tube and an X-ray detector are mounted.

Modification

Hereinafter, a modification of the present embodiment will be described. In the description below, structural elements having substantially the same functions as in the present embodiment are denoted by like reference numerals, and an overlapping description will be given only where necessary.

FIG. 10 is a view illustrating a configuration of an X-ray computed tomography system according to a modification of the present embodiment. As illustrated in FIG. 10, the X-ray computed tomography system according to the modification includes one or a plurality of X-ray computed tomography apparatuses 100, and a scan planning apparatus 200. The one or plural X-ray computed tomography apparatuses 100 and the scan planning apparatus 200 are communicably connected over a network.

The X-ray computed tomography apparatus 100 performs a CT examination according to a scan plan which is created by the scan planning apparatus 200. The X-ray computed tomography apparatus 100 according to the modification has a configuration in which the scan planning function 444 and lift route determination function 445 are excluded from the X-ray computed tomography apparatus 1 of FIG. 1.

The scan planning apparatus 200 is a computer device which generates a scan plan relating to a subject of an examination target, and determines a lift route in the examination.

Figure 11:
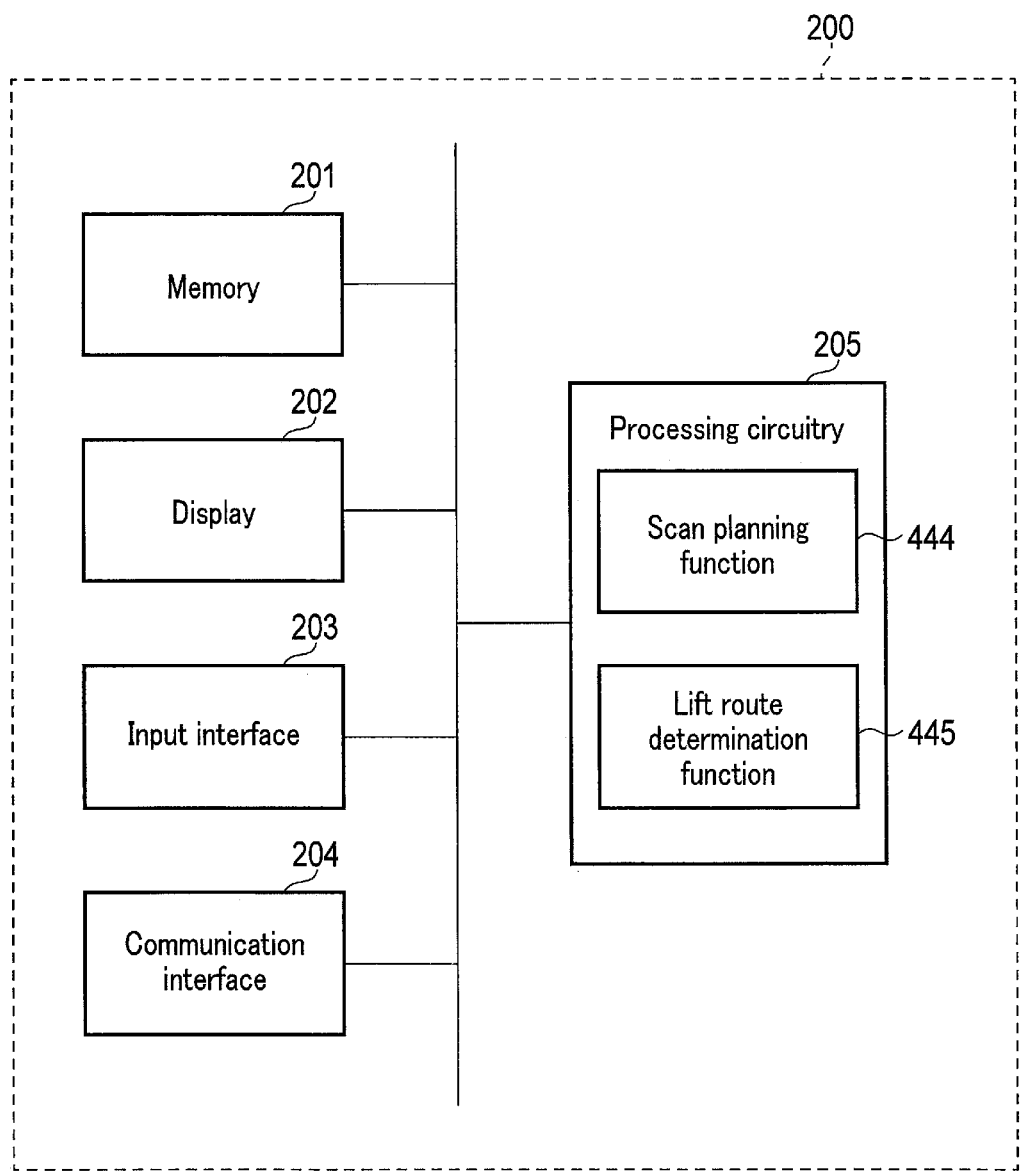
FIG. 11 is a view illustrating a configuration of a scan planning device of FIG. 10.

FIG. 11 is a view illustrating a configuration of the scan planning apparatus 200. As illustrated in FIG. 11, the scan planning apparatus 200 includes a memory 201, a display 202, an input interface 203, a communication interface 204 and processing circuitry 205. Data communication between the memory 201, display 202, input interface 203, communication interface 204 and processing circuitry 205 is executed via a bus (BUS).

The memory 201 is a storage device which stores various information, such as an HDD, an SSD or an integrated circuit storage device. The memory 201 may be, aside from the HDD, SSD or the like, a portable storage medium such as a CD, a DVD, a flash memory or the like, or may be a drive unit which reads/writes various information from/to a semiconductor memory device or the like, such as a RAM.

The display 202 displays various kinds of information. The display 202 outputs, for instance, a scan plan and a lift route generated by the processing circuitry 205, and a GUI or the like for accepting various kinds of operations from the operator. As the display 202, for example, use can be made of, as needed, a liquid crystal display, a CRT display, an organic EL display, a plasma display, or some other discretionarily chosen display.

The input interface 203 accepts various kinds of input operations from the operator, converts the accepted input operations to electric signals, and outputs the electric signals to the processing circuitry 205. As the input interface 203, for example, use can be made of, as needed, a mouse, a keyboard, a trackball, a switch, a button, a joystick, a touchpad, a touch panel display, etc. In the present embodiment, the input interface 203 is not limited to a device including a physical operation part, such as a mouse, a keyboard, a trackball, a switch, a button, a joystick, a touchpad, a touch panel display, etc. Examples of the input interface 203 include processing circuitry of an electric signal, which receives an electric signal corresponding to an input operation from an external input device, which is provided separately from the apparatus, and outputs the received electric signal to the processing circuitry 205.

The communication interface 204 executes data communication with the X-ray computer tomography apparatus 100 by wire or by radio (not illustrated). For example, the communication interface 204 notifies the X-ray computer tomography apparatus 100 of a lift route determined in the lift route determination function 445.

The processing circuitry 205 controls the operation of the entirety of the scan planning apparatus 200 in accordance with an electric signal of an input operation which is output from the input interface 203. For example, the processing circuitry 205 includes, as hardware resources, a processor such as a CPU, an MPU, a GPU, etc., and a memory such as a ROM, a RAM, etc. The processing circuitry 205 executes the scan planning function 444 and lift route determination function 445, by the processor which executes a program developed on the memory. Note that the embodiment is not limited to the case in which the respective functions 444 and 445 are realized by single processing circuitry. Processing circuitry may be composed by combining a plurality of independent processors, and the respective processors may execute programs, thereby realizing the functions 444 and 445.

In the scan planning function 444, like the above-described embodiment, the processing circuitry 205 creates a scan plan automatically or in accordance with an instruction from the operator, which is input via the input interface 203 or the like. The data relating to the scan plan is supplied to the console of the X-ray computed tomography apparatus 100 via the communication interface 204.

In the lift route determination function 445, like the above-described embodiment, the processing circuitry 205 determines the lift route, based on the scan condition, automatically or in accordance with an instruction from the operator, which is input via the input interface 203 or the like. The data relating to the lift route is supplied directly to the gantry 10 of the X-ray computed tomography apparatus 100 via the communication interface 204, or supplied indirectly via the console 40 of the X-ray computed tomography apparatus 100.

Like the above-described embodiment, the control device 15 of the gantry 10, which received the supplied data relating to the lift route, lifts the table top 33 of the bed 30 in accordance with the set lift route.

As described above, according to the modification, the lift route determination function 445 is provided in the scan planning apparatus 200 which is an external apparatus of the X-ray computed tomography apparatus 100. By this configuration, the automatic determination of the lift route can be executed by only providing the lift route determination function 445 in the processing circuitry 205 of the scan planning apparatus 200, without modifying the processing circuitry 44 of the X-ray computed tomography apparatus 100. When there are a plurality of X-ray computed tomography apparatuses 100 in the X-ray computed tomography system, the lift route determination function 445 does not need to be provided in each X-ray computed tomography apparatus 100, and therefore the cost can be reduced.

According to at least one of the above-described embodiments, the flexibility relating to the selection of the lift route of the table top can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical imaging diagnosis apparatus comprising:
   a gantry configured to acquire data;
   a bed configured to support a table top such that the table top is horizontally and vertically movable relative to a floor surface; and
   processing circuitry configured to select, as a lift route of the table top from an initial height to a target height, either a first route or a second route, the first route being in which the table top is vertically lifted relative to the floor surface from the initial height to the target height, the second route being in which the table top is vertically lifted, while being horizontally moved, relative to the floor surface from the initial height to the target height,
   wherein the first route is selected when a scan is a head scan, an external light projector is used, a direction of a subject is head-first, or a stretcher is used.

2. The medical imaging diagnosis apparatus of claim 1, wherein the processing circuitry is configured to select the lift route to be one of the first route and the second route, in accordance with a scan condition or patient information relating to the subject.

3. The medical imaging diagnosis apparatus of claim 2, wherein the scan condition is at least one of, a condition as to whether or not the scan is head scan, a condition relating to presence/absence of use of the external light projector, a condition relating to the direction of the subject on the table top, and a condition relating to presence/absence of use of the stretcher.

4. The medical imaging diagnosis apparatus of claim 2, wherein when a scan condition of a previous examination is included in the patient information relating to the subject of an examination target, the processing circuitry is configured to select the lift route of a present examination, based on the scan condition of the previous examination.

5. The medical imaging diagnosis apparatus of claim 2, wherein when a lift route of a previous examination is included in the patient information relating to the subject of an examination target, the processing circuitry is configured to select the lift route of the previous examination to be the lift route of a present examination.

6. The medical imaging diagnosis apparatus of claim 2, further comprising an interface for selecting one of the first route and the second route,
   wherein the processing circuitry is configured to select the first route as the lift route when the first route is selected via the interface after the lift route was selected in accordance with the scan condition or the patient information, and the processing circuitry is configured to select the second route as the lift route when the second route is selected via the interface after the lift route was selected in accordance with the scan condition or the patient information.

7. The medical imaging diagnosis apparatus of claim 1, further comprising an interface for selecting one of the first route and the second route,
   wherein the processing circuitry is configured to select the first route as the lift route when the first route is selected via the interface, and the processing circuitry is configured to select the second route as the lift route when the second route is selected via the interface.

8. The medical imaging diagnosis apparatus of claim 1, further comprising a display configured to display the selected lift route.

9. The medical imaging diagnosis apparatus of claim 1, wherein the bed includes a support frame configured to support the table top such that the table top is slidable in a long-axis direction of the table top, and a base configured to support the support frame such that the support frame is slidable in the long-axis direction and such that the support frame is vertically movable relative to the floor surface,
   the base is configured to be capable of structurally moving the support frame in the long-axis direction in interlock with a vertical movement of the support frame.

10. The medical imaging diagnosis apparatus of claim 1, wherein the gantry includes an imaging mechanism for X-ray CT scan, MR scan, SPECT scan or PET scan.

11. A scan planning apparatus connected to a medical imaging diagnosis apparatus including a gantry configured to acquire data, and a bed configured to support a table top such that the table top is horizontally and vertically movable relative to a floor surface, the scan planning apparatus comprising:
   processing circuitry configured to select, as a lift route of the table top from an initial height to a target height, either a first route or a second route, the first route being in which the table top is vertically lifted relative to the floor surface from the initial height to the target height, the second route being in which the table top is vertically lifted, while being horizontally moved, relative to the floor surface from the initial height to the target height, wherein the first route is selected when a scan is a head scan, an external light projector is used, a direction of a subject is head-first, or a stretcher is used; and an interface configured to notify the medical imaging diagnosis apparatus of the selected lift route.

12. The scan planning apparatus of claim 11, wherein the processing circuitry is configured to select the lift route to be one of the first route and the second route, in accordance with a scan condition or patient information relating to the subject.

13. The scan planning apparatus of claim 12, wherein the scan condition is at least one of a condition as to whether or not the scan is head scan, a condition relating to presence/absence of use of the external light projector, a condition relating to the direction of the subject on the table top, and a condition relating to presence/absence of use of the stretcher.

14. The scan planning apparatus of claim 11, further comprising an interface for selecting one of the first route and the second route, wherein the processing circuitry is configured to select the first route as the lift route when the first route is selected via the interface, and the processing circuitry is configured to select the second route as the lift route when the second route is selected via the interface.

15. The scan planning apparatus of claim 11, further comprising a display configured to display the selected lift route.

16. The scan planning apparatus of claim 11, wherein the bed includes a support frame configured to support the table top such that the table top is slidable in a long- axis direction of the table top, and a base configured to support the support frame such that the support frame is slidable in the long-axis direction and such that the support frame is vertically movable relative to the floor surface, the base is configured to be capable of structurally moving the support frame in the long-axis direction in interlock with a vertical movement of the support frame.

17. The scan planning apparatus of claim 11, wherein the gantry includes an imaging mechanism for X-ray CT scan, MR scan, SPECT scan or PET scan.

\* \* \* \* \*